United States Patent [19]

Fitch et al.

[11] Patent Number: 5,797,843
[45] Date of Patent: Aug. 25, 1998

[54] ENHANCEMENT OF ORGAN WALL MOTION DISCRIMINATION VIA USE OF SUPERIMPOSED ORGAN IMAGES

[75] Inventors: Geoffrey N. Fitch, McCordsville; Harvey Feigenbaum, Carmel, both of Ind.

[73] Assignee: Eastman Kodak Comapny, Rochester, N.Y.

[21] Appl. No.: 970,904

[22] Filed: Nov. 3, 1992

[51] Int. Cl.$^6$ ................................................. G06F 00/00
[52] U.S. Cl. ................................................. 600/437; 600/442
[58] Field of Search ................. 364/413.13, 413.25; 128/660.01, 660.02, 660.09, 654, 654.07, 654.06, 653.1, 695 R

[56] References Cited

U.S. PATENT DOCUMENTS

| | | |
|---|---|---|
| 4,825,388 | 4/1989 | Dailey et al. |
| 4,855,910 | 8/1989 | Bohning . |
| 4,870,692 | 9/1989 | Zulderveld et al. |
| 5,034,986 | 7/1991 | Karmann et al. |
| 5,035,244 | 7/1991 | Stokar . |
| 5,040,225 | 8/1991 | Gouge . |
| 5,054,045 | 10/1991 | Whiting ................. 358/111 |
| 5,224,481 | 7/1993 | Ishihara et al. ........... 128/660.07 |
| 5,233,993 | 8/1993 | Kawano ................. 128/660.07 |
| 5,241,473 | 8/1993 | Ishihara et al. ........... 364/413.25 |

FOREIGN PATENT DOCUMENTS

| | | | |
|---|---|---|---|
| AT-B-343 734 | 6/1978 | Austria . | |
| 1421306 | 9/1988 | U.S.S.R. | ........... A61B 8/00 |
| WO 91/19457 | 12/1991 | WIPO . | |

OTHER PUBLICATIONS

Pattern Recognition, vol. 18, No. 2 (1985) at pp. 115–124.
IEEE Trans. Biomed. Engr., vol. BME-34, No. 3 (Mar., 1987) pp. 244–247.

*Primary Examiner*—Gail O. Hayes
*Assistant Examiner*—Joe Thomas
*Attorney, Agent, or Firm*—W. Brinton Yorks, Jr.

[57] ABSTRACT

Subtle changes in heart wall motion which may be symptomatic of coronary disease states are more easily discerned by acquiring a real time sequence of ultrasonic diagnostic images. An image acquired at a predetermined point in the cardiac cycle, such as the end diastole image, is chosen as a mask image, and the heart wall in the mask image is colored a first color. The heart wall in the remaining images in the sequence is colored a second, contrasting color. The contrasting images are then successively displayed in overlapping alignment with a static display of the mask images. Abnormalities in heart wall motion are more easily discerned by the relative motion between the contrasting image sequence and the mask image.

18 Claims, 3 Drawing Sheets

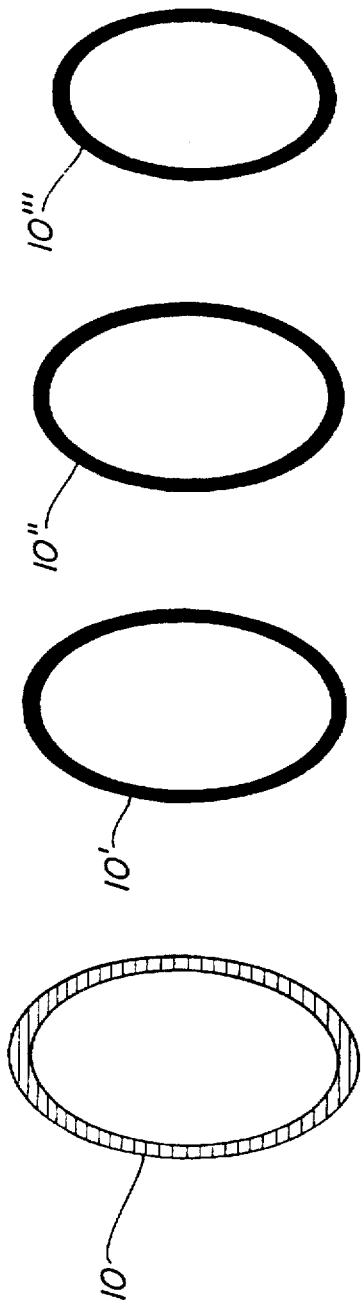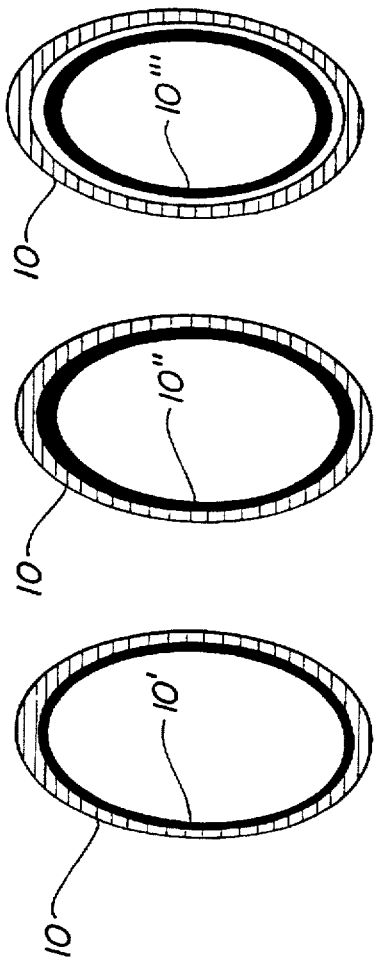

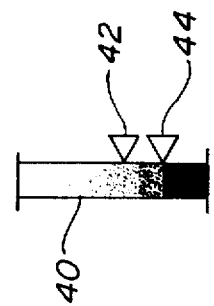
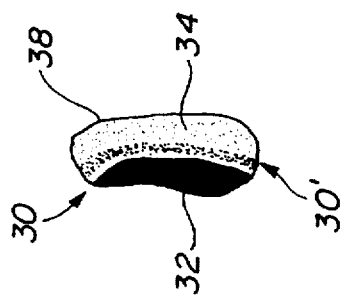
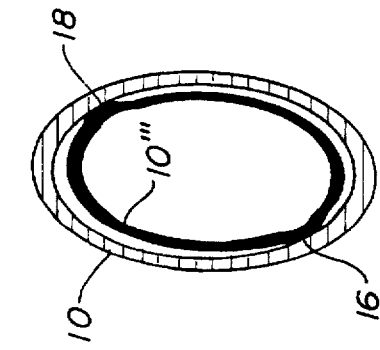
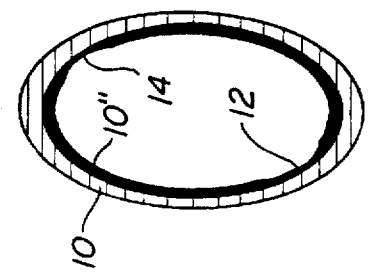
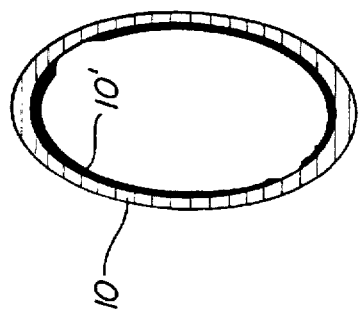
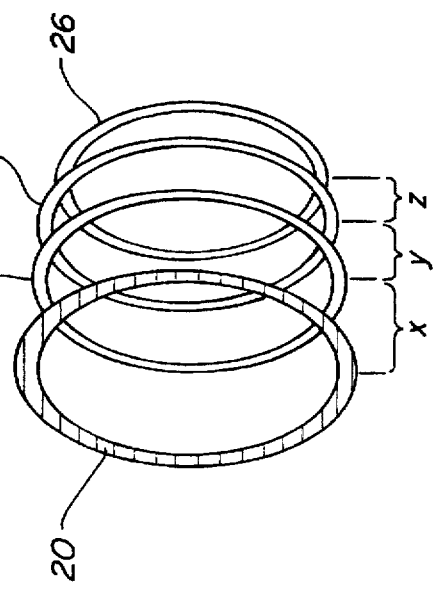

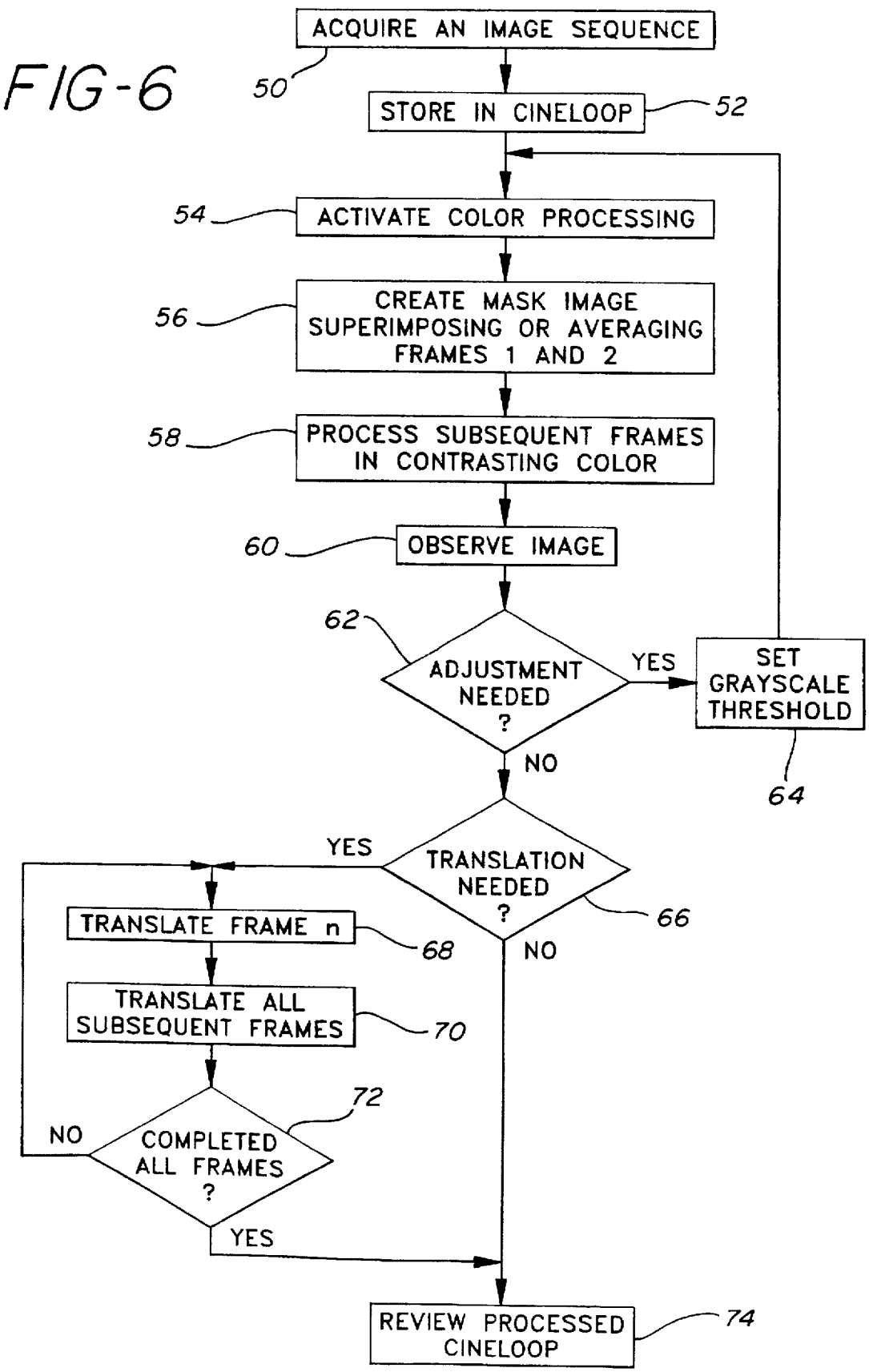

ENHANCEMENT OF ORGAN WALL MOTION DISCRIMINATION VIA USE OF SUPERIMPOSED ORGAN IMAGES

This invention relates to the use of diagnostic imaging systems for the diagnosis of diseases of the heart and other vessels and organs of the body and, in particular, to the use of a sequence of images of internal structure of the body for the identification of infirmities in the health of the heart and other vessels and organs.

Various noninvasive diagnostic imaging modalities are capable of producing sequences of cross-sectional images of organs or vessels which depict the condition of such vessels or organs during sequential phases of their operation. An imaging modality which is well suited for such real-time noninvasive imaging is ultrasound. Ultrasonic diagnostic imaging systems are in widespread use for performing ultrasonic imaging and measurements through the use of scanheads which are placed against the skin. Such systems are in common use by radiologists, cardiologists, and obstetricians for examinations of the heart, a developing fetus, or internal abdominal organs. These systems operate by transmitting waves of ultrasonic energy into the body, receiving echoes returned from tissue interfaces upon which the waves impinge, and translating the received echo information into structural representations of the planar "slice" of the body through which the ultrasonic waves are directed.

The ability of ultrasonic diagnostic systems to rapidly produce sequences of images of the cardiovascular system has been especially useful in the practice of cardiology. Cardiologists can rapidly and easily acquire a sequence of images during the cardiac cycle, which can be viewed in real time or stored in Cineloop™ memory for subsequent review, at which time the entire sequence can be replayed at various speeds or individual images examined.

A disease state that can be accurately diagnosed by these means is myocardial infarction or heart attack. The cardiologist will image the heart wall or myocardium to dynamically detect changes in contraction brought about by an ischemic event as a result of coronary artery occlusion. These changes in myocardial motion may range from subtle disturbances in contractility to total akinesia. Differentiating subtle heart wall motion abnormalities arising from partial obstructions are often more difficult than those reflecting changes from complete occlusion.

Echocardiographic imaging has traditionally utilized greyscale imaging techniques, particularly those which provide scan formats capable of imaging the heart transthoracically, through the ribs. In a greyscale presentation, tissue structure is represented in varying shades of grey. Color imaging is a relatively recent tool for cardiologists, and has in recent years been utilized in color Doppler imaging where blood flow velocities are represented in varying hues of color. Structure continues to be shown in greyscale. But the interest in color imaging has been present for two decades. In the early 1970's color was first used to show structure, with hues of color used in place of the shades of grey of the greyscale image. See, e.g., Kossoff, G., "Display techniques in ultrasound pulse echo investigations: a review", J. Clin. Ultrasound 2: 61–72 (1974). This utilization of color was said to be an improvement, in that the human eye was said to perceive finer gradations of color than shades of gray This claim has been disputed over the years, and it was not until the decade of the 1990's that such implementations became routinely commercially available. Color presentations of tissue structure which provide a distinct clinical advantage have been an elusive objective, at best.

In accordance with the principles of the present invention, subtle changes in heart wall motion which may be symptomatic of partial coronary artery occlusion are enhanced by first acquiring a sequence of images of the heart during the cardiac cycle. A particular point in the cardiac cycle is denominated as a reference, such as the start of the cycle. One or more image frames acquired during the reference point in the cardiac cycle are utilized to produce a mask image which is given a unique visual appearance, such as coloring the heart wall of the mask image a first color. The succeeding image frames of the sequence are given a contrasting visual appearance, such as coloring the heart wall with a second color. The mask image is displayed on a screen and the succeeding image frames are then displayed in sequence in the display background. The heart wall motion in the subsequent frames will then be seen to move in relation to the mask image, enabling changes in wall motion to be more easily distinguished.

In accordance with another aspect of the present invention, cognizance is taken of the fact that the heart will also translate in position in the chest cavity as it beats. The present invention accounts for this condition by allowing the subsequent images to be translated to the position of the mask image when they are reviewed.

In accordance with yet a further aspect of the present invention, it is recognized that accurate delineation of the tissue of the heart wall will facilitate a more accurate diagnosis. Accordingly, selection of the area of an image which is to be highlighted in contrast to the mask image or the succeeding images is performed by defining the limits of a range of pixel intensities in the initial greyscale image which are to be contrasted. By changing the range limits the user can adjust the display to accurately delineate the heart wall over a wide variety of conditions of ultrasonic signal reception, processing and image display.

In the drawings:

FIGS. 1a through 1c schematically illustrate a sequence of four images of the heart taken during a cardiac cycle;

FIGS. 2a through 2c schematically illustrate the masking of the images of FIGS. 1b–1c by the image of FIG. 1a in accordance with the principles of the present invention;

FIGS. 3a through 3c schematically illustrate the masking of sequential images of a heart with wall motion abnormalities;

FIG. 4 illustrates the relocation of images of a translating heart;

FIGS. 5a and 5b illustrate the selection of the greyscale area of an image for contrast enhancement in accordance with the principles of the present invention; and FIG. 6 is a flowchart of the implementation of various features of the present invention for an ultrasound image workstation.

The sequence of images of FIGS. 1a–1c schematically depicts a sequence of images of the heart taken during one heart cycle. For ease of illustration the heart has been schematically represented as an oval. The structure of the heart depicted in the drawings is the myocardium or wall of the heart.

In a preferred application of the present invention a sequence of images of the heart are acquired by an ultrasonic diagnostic imaging system. Each image shows a cross-sectional view of the heart along the plane on which the ultrasonic energy is transmitted through the heart. As is well known, such images may be acquired by use of either a transthoracic scanhead which transmits energy into the body from outside the body, or a transesophageal scanhead positioned within the esophagus. Ultrasonic cardiac images are conventionally acquired and displayed at a rate of approximately 30 frames per second. Thus, sixteen to thirty-two frames could be acquired during a single heart cycle in most cases. The present inventors have found that diagnostically useful information can be determined from an eight frame sequence, and accordingly it is their practice to capture and store in image memory a sequence of eight frames. Each successive frame shows the heart at a successively later phase in the cardiac cycle of contraction and expansion. The clinician may review the continuing display of successive images by activating what is known as the Cineloop™ memory of the system. When activated, the Cineloop memory will display the predetermined number of frames which have been saved. A typical Cineloop memory can store from 64 to 128 successive frames.

FIG. 1a depicts the heart wall 10 at the very beginning of the cardiac cycle, just before the heart begins its systolic (contraction) phase. This is a preferred reference image for the present invention because the heart is fully expanded at this point of its cycle. This point in the heart cycle is also referred to as end diastole, the end of the heart's relaxive period. The clinician can locate an end diastole image by acquiring an image sequence which is several heart cycles in length, then looking through the sequence until an expansive end diastole image is located. This search may be automated by utilizing an EKG trigger to acquire an image sequence. Since the R-wave trigger of the EKG signal defines end diastole, the R-wave trigger can be used to automatically trigger the Cineloop memory to begin storing successive images, with the first image stored being end diastole. The end diastole image is then used as the basis for the reference, or mask image which is used with a number of successive frames in accordance with the present invention. The total number of successive frames processed in accordance with the invention is preferably eight, for instance.

Preferably the end diastole frame is not used alone, but is digitally averaged or combined with the next successive frame. This is because ultrasound images at end diastole often exhibit signal dropout, and the averaging or combining will fill in image regions experiencing dropout. Alternatively, two successive image frames may be examined on a pixel by pixel basis, and the maximum signal value of the two at each pixel location is used in a consolidated, or superimposed frames The averaged or superimposed frame is used as the mask image. In a case where signal dropout is not a problem the averaging or superimposition of frames may be omitted.

The mask image is highlighted so as to contrast with the rest of the image frames in the sequence. This may be accomplished by giving the heart wall in the mask frame a distinctive brightness, hue or shading. In a preferred embodiment the heart wall of the mask frame is given a distinctive color such as blue. The blue colorizing of the heart wall 10 is represented by the horizontally lined oval in FIG. 1a.

When the end diastole image is used to produce the mask frame, the successive images will show the heart contracting as it proceeds through its systolic phase. Hence the ovals of FIGS. 1b–1d are drawn smaller than the oval of FIG. 1a, although that may not be readily apparent from the individual drawings. In accordance with the present invention these successive images are given a contrasting appearance in brightness, hue or shading. In the preferred embodiment the heart wall 10 of these successive images are colored red. The red coloring is depicted by the dark shading in FIGS. 1b through 1d.

In a review of these images in accordance with the present invention, the mask image of FIG. 1a is displayed continuously on the screen, and successive images are successively displayed overlaid with the mask image. In the preferred embodiment the mask image is displayed in the foreground as the dominant image and the successive images are displayed in the background. This display enables the clinician to view the motion of the heart wall over a succession of images in constant relation to the reference mask image. Thus, FIG. 2a shows the concurrent display of the FIG. 1a and FIG. 2a images. Since the heart is just beginning to contract in FIG. 1b, the heart wall 10' is just beginning to appear inside the contrasting heart wall 10 of the mask image. FIG. 2b shows the mask image displayed with the next successive image of FIG. 1c, and the heart wall 10" is seen to be making a greater appearance inside the mask image heart wall 10. FIG. 2c, which shows the concurrent display of the FIG. 1d image with the mask image, shows the heart wall 10'" now fully inside the heart wall 10 of the mask image.

In the operation of a normal healthy heart, the edge of the contracting heart wall will begin to appear evenly inside the heart wall 10 of the mask image. FIGS. 3a–3c depict the operation of a heart where areas of the wall move unevenly or lethargically as a result of coronary artery occlusion. FIG. 3a shows the first successive image 10' initially appearing unevenly inside the boundary of the mask image wall 10. As the drawing begins to reveal, there are areas of uneven motion at the upper right and lower left of the oval. In FIG. 3b the next successive image makes these area 12 and 14 of uneven motion even more apparent. In FIG. 3c the later successive image again highlights the uneven motion, as the wall 10'" of the later image is touching the mask image wall 10 at areas 14 and 16 after the rest of the contracting heart wall 10'" has moved inside the boundary of the mask image 10.

By displaying the images of the sequence in concert with the fixed mask image at display rates up to real time, the dynamics of variations in heart wall motion are viewed in relation to the heart wall position in the mask image, enabling the detection of subtle abnormalities in the performance of the heart. The patient can then be appropriately treated for any suspected partial occlusion of the coronary artery system.

In many patients the heart does not simply expand and contract about a fixed central point of the organ. Rather, the heart itself will translate in its entirety within the chest cavity as it beats. Through observation clinicians have recognized that in certain apical views the heart should appear to move up and down but not right-to-left. In particular, as the heart muscle contracts, the annulus around which the mitral valve is attached should appear to move up and down but not right-to-left in these views. Accordingly it is desirable to correct for any right-to-left translation of the heart annulus in such images before using the sequence of images for diagnosis.

FIG. 4 illustrates the effect of such heart translation on an image sequence. From the resting position of mask image 20, the heart could move laterally as it contracts to a subsequent position shown by the next heart wall image 22. The new position is displaced from the initial position by an increment x. As the heart continues to contract it could move even further to the right, as indicated by subsequent images 24 and 26. The position of the heart wall in image 24 is displaced from the position of the heart wall in image 22 by a further incremental position y, and the position of the heart wall moves a further increment z by the time of acquisition of image 26. Since this translational movement and resultant disruption of concentric alignment of the heart wall images will have a deleterious effect upon the diagnostic efficacy of the display of overlaid images, the preferred embodiment of the present invention provides for correction of the translational effect. With the first or mask image 20 statically displayed on a screen, the next image 22 in the sequence is concurrently displayed. A control such as a key, a joystick, or a trackball is manipulated to move the heart wall of image 22 to the left by the increment x, bringing the two heart wall images into approximate concentric alignment. As the image 22 is moved, the subsequent images in the sequence are all adjusted by the same amount. Thus, if the sequence comprised a total of eight images, as the second image is aligned with the first image, images three through eight would all be moved by the increment x. When the first and second images have been aligned, the second image 22 is statically displayed concurrently with the third image 24. Since the heart walls of these two images are misaligned by the increment y, the control is used to correct the position of the heart wall of image 24 by this further increment. As before, the remaining images in the sequence are automatically relocated by the increment y. The image 26 is then adjusted by the increment z to bring it into alignment with image 24, in the same manner. At this point, all four images of FIG. 4 have been aligned, image 22 by the increment x, image 24 by the increment x+y, and image 26 by the increment x+y+z, and all subsequent images in the sequence have been corrected by the total increment of x+y+z. After all eight images in the above example have been aligned in this manner, each stored image is tagged with a display parameter which is the cumulative adjustment to be used in the display of the associated image. The full sequence can be reviewed as above and the diagnosis performed.

It may be appreciated that while the above example of translational correction involves only a simple adjustment in horizontal positioning, correction in a particular embodiment may involve relocation in any direction in the Cartesian coordinate plane of the image, or angular or rotational correction of image position.

As it is the purpose in the illustrated embodiments to display specific tissue in contrasting appearances so as to detect subtle differences in the motion of the tissue, it may be appreciated that consistent identification of the tissue and its boundaries from image to image is important. It would be undesirable to extend the colorizing in the image beyond or short of the actual physical boundary of the heart wall muscle. In accordance with a further aspect of the present invention, a consistent means is provided for colorizing or contrasting that part of the diagnostic image which is identified as the heart wall muscle. Referring to FIG. 5a, a portion 38 of a diagnostic image of the heart wall is shown. The band of moderate grey between arrows 30–30' represents the cross-sectional display of the heart wall. Inside the heart wall is a dark area 32 which is the display of blood inside the heart. Outside the heart is a lighter grey area 34 of soft tissue. A clinician viewing this image statically can distinguish the moderate grey area of the heart wall and will recognize that the display pixels in this area are to be colorized or contrasted in use of the present invention. To select the band of grey between arrows 30–30' for colorizing, the user views a concurrently displayed greyscale bar 40 as shown in FIG. 5b. The greyscale bar 40 continuously varies in greyscale shading from the darkest shade to the lightest shade of the image. The clinician then adjusts two slide controls on the system which move upper and lower pointers 42 and 44 along the greyscale bar. The pointers are adjusted until the band of the greyscale between them is the same as the grey shading of the heart wall in the image. When the clinician believes that the pointers are properly set, the command is given to colorize the heart wall in accordance with the range of grey defined between the upper and lower pointers.

The colorized image is then carefully inspected to determine that only the heart wall area of the display has been colorized and that the color does not extend beyond the heart wall pixels in the image. Some further adjustment of the slide controls may then be performed until the colorized area accurately defines the heart wall. The selected range of grey between the pointers is then used to colorize the heart wall on all of the images in the sequence. By reviewing the images and making further adjustment to the pointers 42 and 44 the colorization is finely adjusted to accurately colorize the heart wall even in the presence of varying or weak ultrasonic signal conditions.

In a preferred embodiment of the present invention the parameters controlled by the slide controls and their pointers 42 and 44 are as follows. Pointer 44 defines a greyscale pixel intensity level below which pixels are eliminated from the mask image. The effect of this control is to remove clutter and distractive artifacts from the mask image. This low level pixel elimination effect can also be applied to the underlying images, if desired. Pixels having intensities ranging above the level of the upper pointer 42 are given a constant mask intensity value. Pixels having intensities ranging between the two pointer levels are given color intensities in accordance with their greyscale intensity values, thereby preserving the structural tissue characteristics of the heart wall image.

In some imaging applications the heart wall muscle will expectedly be displayed with the highest intensity in the image. In such an application only a single threshold need be set, above which the image is colored to distinguish the heart wall and below which it is not colored. When the clinician views such an image, a single control such as a slide bar, arrow or function key or numerical threshold value is changed to color more or fewer pixels as the heart wall. The control is manipulated until the clinician is satisfied as to the allocation of distinguishing color to the heart wall muscle in the mask image.

If desired, a second bar similar to greyscale bar 40 can be displayed, the second bar displaying a spectrum of colors. The second bar would have two pointers similar to those of bar 40. In the case of the color bar, a first pointer designates the color to be used for the mask image and a second pointer designates the contrasting color to be used for all of the subsequent images in the sequence. The color intensities may then be modulated as described above.

It is further understood that many ultrasound systems also allow the user to vary the entire greyscale range in which images are displayed, and the foregoing selection of colorized shades may be performed in concert with greyscale adjustment of the entirety of each image in the full sequence.

FIG. 6 illustrates the flowchart of an implementation of the diagnostic enhancement technique of the present invention for an Imagevue™ or ImageVue DCR™ workstation available from Nova MicroSonics of Mahwah, New Jersey. At the starting block 50 in the flowchart a sequence of cardiac images is acquired from a video source. The video source could be a videotape on which a sequence of cardiac images has been recorded. The video source could also be the image data port of an ultrasound system which is acquiring the image sequence in real time, such as an Ultramark 9 HDI™ ultrasound system available from Advanced Technology Laboratories, Inc. of Bothell, Washington. In either case the images of the sequence are acquired by a video frame grabber and stored in Cineloop® memory in the workstation. The ImageVue DCR workstation has a Cineloop memory with a capacity of 64 megabytes, which is capable of storing approximately one thousand image frames. Since a full cardiac cycle can generally be represented by approximately thirty frames, a smaller Cineloop memory may also be adequate for other applications In block 54 the color processing of the image sequence is activated by the workstation's operating program. The first operation is to create the mask image. An enhanced image is created by the averaging or superimposition of the first two frame of the image sequence, starting from the chosen reference in the cardiac cycle such as end diastole. The heart wall of the enhanced image is then colored blue as described previously. In block 58 the subsequent frames in the image sequence are distinguished by coloring the heart wall in those frames red.

In block 60 the user observes the images, generally starting with the mask image, to determine if any adjustment in heart wall definition is needed as indicated by decision block 62. If the definition of the heart wall is not acceptable, the grayscale threshold pointers of FIG. 5b are adjusted and the color processing sequence is repeated with the heart wall colorized in accordance with the new threshold settings as previously described.

Once the heart wall in the images is clearly defined, the workstation proceeds to decision block 66, which poses the question of the need for translation. If the user decides that translation of the image is needed in order to compensate for motion of the heart within the chest cavity, the frame following the mask image is translated into alignment with the heart wall in the mask image as described above. This operation is represented by block 68, starting with frame n where n is equal to two. Alignment of the second frame automatically results in corresponding translation of the subsequent frames as shown by block 70. This translation process continues until all n frames in the sequence have been brought into alignment as indicated by the loop to block 68 from decision block 72. The processed image sequence is now available for review by the user as indicated by block 74.

What is claimed is:

1. A method for distinguishing motional characteristics of moving tissue within the body comprising the steps of:
    a) acquiring a sequence of images of said tissue during a period of its motional activity;
    b) coloring tissue represented in a first image in the sequence in a first color;
    c) coloring tissue represented in the other images in the sequence in a second color which is distinguishable from said first color; and
    d) successively displaying said other images in the sequence behind the tissue of said first image to view the motion of said moving tissue in constant relation to said tissue of said first image.

2. The method of claim 1, wherein step d) further comprises the step of concurrently displaying said first image in overlapping tissue alignment, when overlap occurs, with each of said other images.

3. The method of claim 1, wherein said moving tissue comprises the wall of a beating heart, and wherein said first image represents a cross-sectional view of said beating heart at a predetermined point in the heart cycle.

4. The method of claim 3, wherein said predetermined point in the heart cycle comprises end diastole.

5. The method of claim 1, wherein said sequence of images of step a) are acquired ultrasonically.

6. A method for distinguishing displayed notional characteristics of moving tissue within the body comprising the steps of:
    a) acquiring a sequence of ultrasonic images of said tissue on a real time image display during a period of its motional activity;
    b) coloring tissue represented in a first image in the sequence in a first color;
    c) coloring tissue represented in the other images in the sequence in a second color which is distinguishable from said first color; and
    d) statically displaying said first image on a real time image display while displaying said other images in sequence on said display behind said first colored tissue to view the motion of said moving tissue in constant relation to said tissue of said first image, wherein said first and second colors are distinguishable from the background of said displayed tissue.

7. The method of claim 6, wherein step a) comprises the step of ultrasonically acquiring a sequence of greyscale images of said tissue during a period of its motional activity; and comprising the further step of e) selecting a range of greyscale shades which are to be colored.

8. A method for distinguishing motional characteristics of a beating heart within the body comprising the steps of:
    a) ultrasonically acquiring a sequence of images of the beating heart during a portion of the heart cycle;
    b) substantially concentrically aligning each of the heart images with respect to at least one other heart image in the sequence;
    c) coloring tissue represented in a first image in the sequence in a first color;
    d) coloring tissue represented in the other images in the sequence in a second color which contrasts with said first color; and
    e) successively displaying each of said second colored images in substantial tissue alignment behind the tissue of said first image to view the motion of the heart tissue in constant relation to said tissue of said first image.

9. The method of claim 8, wherein step b) comprises the step of positionally translating each of the other heart images in said sequence into improved overlapping heart tissue alignment with the heart tissue of a selected one of said heart images.

10. The method of claim 9, wherein the translation of one of said other heart images into improved overlapping alignment with said selected one of said heart images also effects an improvement in the overlapping alignment of at least one other heart image with said selected one of said heart images.

11. Processing apparatus for presenting diagnostic cardiac images comprising:
    means for acquiring a sequence of ultrasonic cardiac images depicting a cycle of heart motion;
    means for creating a mask image in response to one or more of said ultrasonic cardiac images in which the heart wall is represented in a first color;
    means for representing the heart wall in a plurality of other images in the sequence in a second color which contrasts with the color of the heart wall in said mask image,
        wherein said first and second colors further contrast with the background of the concurrent presentation of said mask image with one of said contrasting images; and means for displaying said plurality of other images in a real time sequence behind the heart wall of said mask image to view the motion of the heart wall in constant relation to said mask image.

12. The processing apparatus of claim 11, further comprising means for determining the portions of said acquired images of said sequence which are to be represented in contrasting visual appearance.

13. The processing apparatus of claim 12, wherein said means for acquiring acquires a grayscale cardiac image sequence, and wherein said means for determining designates a range of grayscale intensities which are to be represented in color.

14. The processing apparatus of claim 11, further comprising means for translating the heart wall representation of images subsequent in the sequence to said mask image into alignment with the heart wall representation of said mask image.

15. A method for distinguishing motional characteristics of the heart wall within the body comprising the steps of:

a) acquiring a sequence of images of said heart wall during a period of its motional activity which includes at least a portion of the systolic phase;

b) denominating a selected image in the sequence as a reference image;

c) coloring heart wall tissue shown in said selected image in a visual appearance which visually contrasts said heart wall tissue from the background of the concurrent display of said selected image with another image in said sequence;

d) coloring heart wall tissue shown in a plurality of other images in the sequence in a contrasting visual appearance which contrasts with the heart wall tissue of said selected image and with the background of the concurrent display of one of said images with a contrasting visual appearance with said selected image; and e) concurrently displaying said selected image with a sequence of said other contrasting images with the heart wall tissue of said selected image in an at least partially overlapping alignment with the heart wall tissue of said other images to view the motion of the heart wall in constant relation to said reference image.

16. The method of claim 15, wherein step d) comprises the step of providing heart wall tissue shown in a plurality of other images in the sequence with a contrasting visual appearance and wherein step e) comprises the step of concurrently displaying said selected image with each of said contrasting images in sequence.

17. The method of claim 16, wherein said sequence of contrasting images is displayed as a substantially real time sequence.

18. The method of claim 15, wherein step c) comprises the step of coloring the heart wall tissue shown in said selected image with a first color or hue which contrasts with the background of the images when concurrently displayed and wherein step d) comprises the step of coloring the heart wall tissue shown in the other images in the sequence with a color or hue which contrasts with said first color or hue and with the background of the images when concurrently displayed.

* * * * *